United States Patent [19]
Brown et al.

[11] Patent Number: 6,071,423
[45] Date of Patent: Jun. 6, 2000

[54] METHODS OF COLLECTING A BLOOD PLASMA CONSTITUENT

[75] Inventors: Richard I. Brown, Northbrook; Sidney Smith, Lake Forest; David E. Cerny, Crystal Lake; John T. Foley, Wheeling, all of Ill.

[73] Assignee: Baxter International Inc., Deerfield, Ill.

[21] Appl. No.: 09/222,751

[22] Filed: Dec. 29, 1998

Related U.S. Application Data

[62] Division of application No. 08/943,750, Oct. 3, 1997, Pat. No. 5,849,203, which is a division of application No. 08/593,719, Jan. 29, 1996, Pat. No. 5,693,232, which is a division of application No. 08/199,082, Feb. 22, 1994, Pat. No. 5,494,578, which is a division of application No. 07/748,244, Aug. 21, 1991, Pat. No. 5,322,620, which is a continuation of application No. 07/514,995, May 26, 1989, Pat. No. 5,104,526, which is a continuation of application No. 07/009,179, Jan. 30, 1987, Pat. No. 4,834,890.

[51] Int. Cl.$^7$ ............................. B01D 21/26; A61M 1/38
[52] U.S. Cl. .................. 210/782; 210/787; 210/789; 210/805; 210/806; 494/37; 604/4; 604/5; 604/6
[58] Field of Search .................................. 210/767, 782, 210/787, 789, 805, 806; 494/37; 604/4, 5, 6

[56] References Cited

U.S. PATENT DOCUMENTS

| | | |
|---|---|---|
| Re. 29,738 | 8/1978 | Adams . |
| 1,931,508 | 10/1933 | Reese et al. . |
| 3,285,507 | 11/1966 | Shapiro . |
| 3,655,123 | 4/1972 | Judson et al. ............... 604/6 |
| 3,708,110 | 1/1973 | Unger et al. ................ 604/6 |
| 3,737,096 | 6/1973 | Jones et al. ................ 494/45 |
| 3,955,755 | 5/1976 | Breillat, Jr. et al. . |
| 4,007,871 | 2/1977 | Jones et al. ............... 210/789 |
| 4,010,894 | 3/1977 | Kellogg et al. ............ 494/18 |
| 4,086,924 | 5/1978 | Latham, Jr. ................ 604/6 |
| 4,094,461 | 6/1978 | Kellogg et al. ............ 494/81 |
| 4,109,854 | 8/1978 | Brown ....................... 494/18 |
| 4,109,855 | 8/1978 | Brown et al. ............... 494/18 |
| 4,146,172 | 3/1979 | Cullis et al. ............... 494/17 |
| 4,164,318 | 8/1979 | Boggs ....................... 494/18 |
| 4,187,979 | 2/1980 | Cullis et al. ............... 494/37 |
| 4,230,263 | 10/1980 | Westberg ................... 494/45 |
| 4,245,383 | 1/1981 | Boggs ....................... 29/428 |
| 4,246,107 | 1/1981 | Takenaka et al. .......... 210/806 |

(List continued on next page.)

FOREIGN PATENT DOCUMENTS

| | | |
|---|---|---|
| 873494 | 7/1961 | United Kingdom . |
| 2002266 | 2/1982 | United Kingdom . |

*Primary Examiner*—John Kim
*Attorney, Agent, or Firm*—Daniel D. Ryan; Bradford R. L. Price

[57] ABSTRACT

A system and method of separation of therapeutic components from blood. The system includes a dual member centrifuge and a disposable single use fluid transfer set. The set includes an elongated flexible separation chamber having an input port, a separated component output port and a residual fluid output port. The input port and the separated component output ports are located at opposite ends of the elongated separation chamber. The centrifuge includes a receiving chamber with a selectively formed annular slot therein. The separation chamber is positioned in the annularly shaped slot and rotated at a predetermined rotational velocity. Fluids such as whole blood flows through the separation chamber and are separated into various therapeutic components such as platelet rich plasma and residual concentrated red blood cells. Platelet rich plasma can be drawn off as the separated therapeutic component. An alternate two part transfer set provides for highly efficient platelet pheresis. The platelet rich plasma is separated from the residual red blood cells in a first part. The platelet rich plasma flows into the second part and is separated into platelet poor plasma and platelets. The platelet poor plasma can be drawn off and returned to a donor or collected. The platelet concentrate can then be accumulated in a separate container.

8 Claims, 10 Drawing Sheets

U.S. PATENT DOCUMENTS

| | | | |
|---|---|---|---|
| 4,261,507 | 4/1981 | Baumler | 494/45 |
| 4,278,202 | 7/1981 | Westberg | 494/45 |
| 4,303,193 | 12/1981 | Latham, Jr. | 604/6 |
| 4,304,357 | 12/1981 | Schoendorfer | 494/21 |
| 4,344,560 | 8/1982 | Iriguchi et al. | 210/787 |
| 4,350,283 | 9/1982 | Leonian | 422/72 |
| 4,356,958 | 11/1982 | Kolobow et al. | 494/43 |
| 4,386,730 | 6/1983 | Mulzet | 494/45 |
| 4,387,848 | 6/1983 | Kellogg et al. | 494/81 |
| 4,402,680 | 9/1983 | Schoendorfer | 494/17 |
| 4,405,079 | 9/1983 | Schoendorfer | 494/1 |
| 4,409,820 | 10/1983 | Nash | 73/61.4 |
| 4,412,831 | 11/1983 | Avery et al. | 494/46 |
| 4,413,771 | 11/1983 | Rhode et al. | 494/17 |
| 4,413,772 | 11/1983 | Rhode et al. | 494/17 |
| 4,413,773 | 11/1983 | Rhode et al. | 494/17 |
| 4,416,654 | 11/1983 | Schoendorfer et al. | 494/10 |
| 4,416,777 | 11/1983 | Kuroda et al. | 210/446 |
| 4,417,884 | 11/1983 | Schoendorfer et al. | 494/4 |
| 4,419,089 | 12/1983 | Kolobow et al. | 494/45 |
| 4,421,503 | 12/1983 | Lathan, Jr. et al. | 494/17 |
| 4,430,072 | 2/1984 | Kellogg et al. | 494/45 |
| 4,439,178 | 3/1984 | Mulzet | 494/85 |
| 4,447,221 | 5/1984 | Mulzet | 494/45 |
| 4,464,167 | 8/1984 | Schoendorfer et al. | 604/6 |
| 4,474,568 | 10/1984 | Schoendorfer et al. | 604/4 |
| 4,482,342 | 11/1984 | Leuptow et al. | 494/21 |
| 4,493,691 | 1/1985 | Calari | 494/10 |
| 4,522,494 | 6/1985 | Bonner | 356/39 |
| 4,525,155 | 6/1985 | Nilsson | 494/3 |
| 4,530,691 | 7/1985 | Brown | 494/45 |
| 4,531,932 | 7/1985 | Luppi et al. | 494/18 |
| 4,557,719 | 12/1985 | Neumann et al. | 494/37 |
| 4,577,964 | 3/1986 | Hansen, Jr. | 356/39 |
| 4,604,086 | 8/1986 | Benko | 494/16 |
| 4,617,009 | 10/1986 | Ohlin et al. | 494/37 |
| 4,624,567 | 11/1986 | Dick et al. | 356/335 |
| 4,636,193 | 1/1987 | Cullis | 494/45 |
| 4,647,279 | 3/1987 | Mulzet et al. | 494/45 |
| 4,670,002 | 6/1987 | Koreeda et al. | 494/10 |
| 4,708,712 | 11/1987 | Mulzet | 494/45 |
| 4,724,317 | 2/1988 | Brown et al. | 494/10 |
| 4,734,089 | 3/1988 | Cullis | 494/97 |
| 4,806,252 | 2/1989 | Brown et al. | 210/744 |
| 4,820,256 | 4/1989 | Nordstrom | 494/3 |
| 4,830,510 | 5/1989 | Bellhouse | 604/410 |
| 4,834,890 | 5/1989 | Brown et al. | 210/739 |
| 4,846,780 | 7/1989 | Galloway et al. | 494/3 |
| 4,934,995 | 6/1990 | Cullis | 494/45 |
| 5,006,103 | 4/1991 | Bacehowski et al. | 494/45 |
| 5,071,570 | 12/1991 | Shiraki et al. | 210/782 |
| 5,089,146 | 2/1992 | Carmen et al. | 210/782 |
| 5,102,407 | 4/1992 | Carmen et al. | 604/410 |
| 5,494,578 | 2/1996 | Brown et al. | 494/45 |

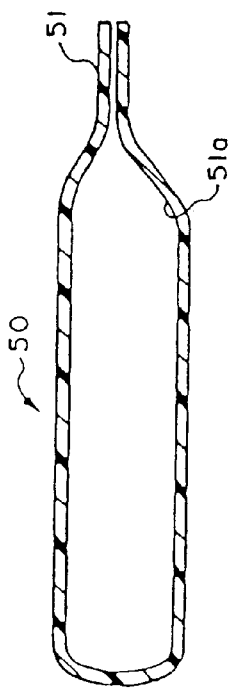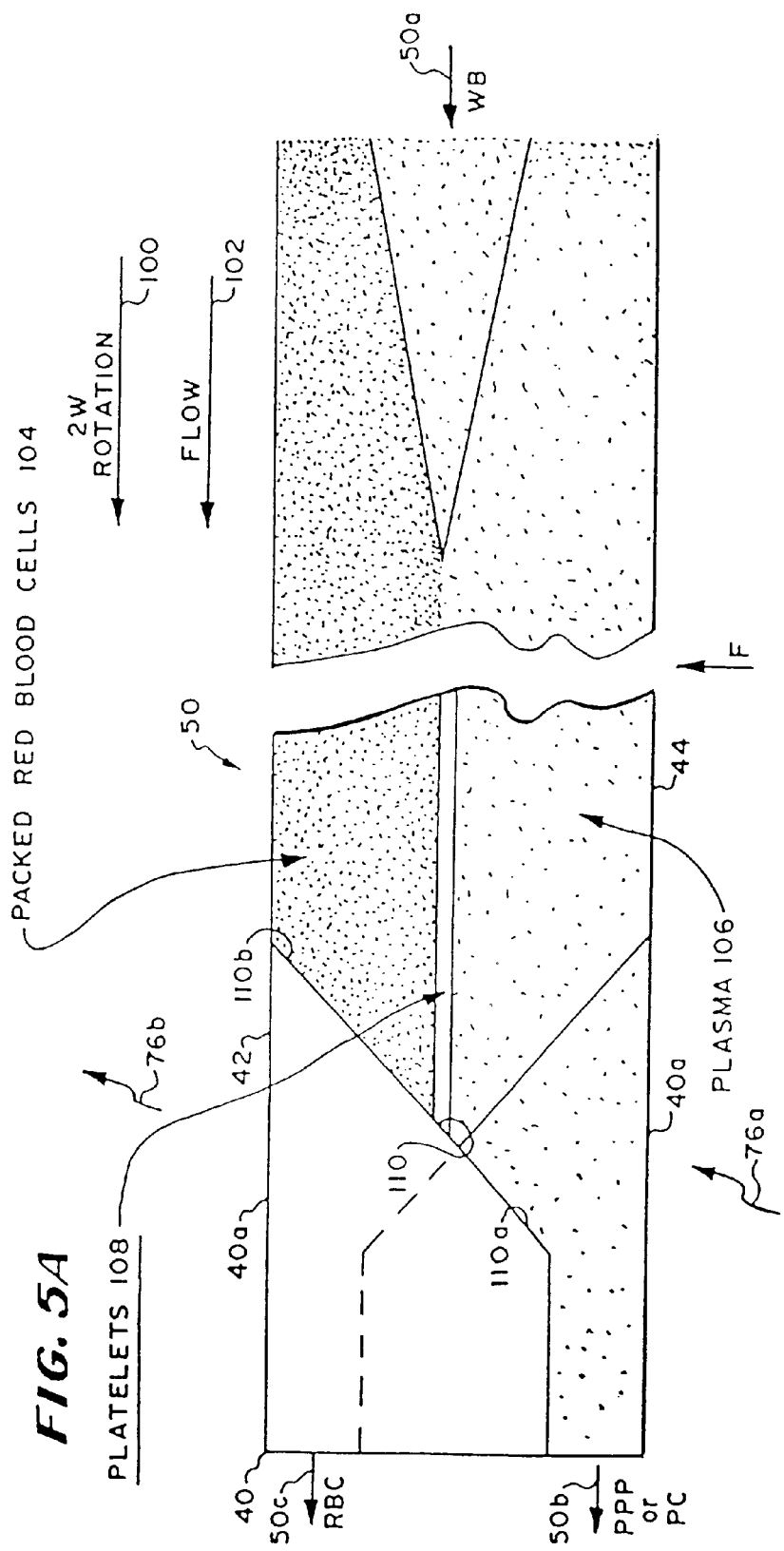
FIG. 4
FIG. 5A

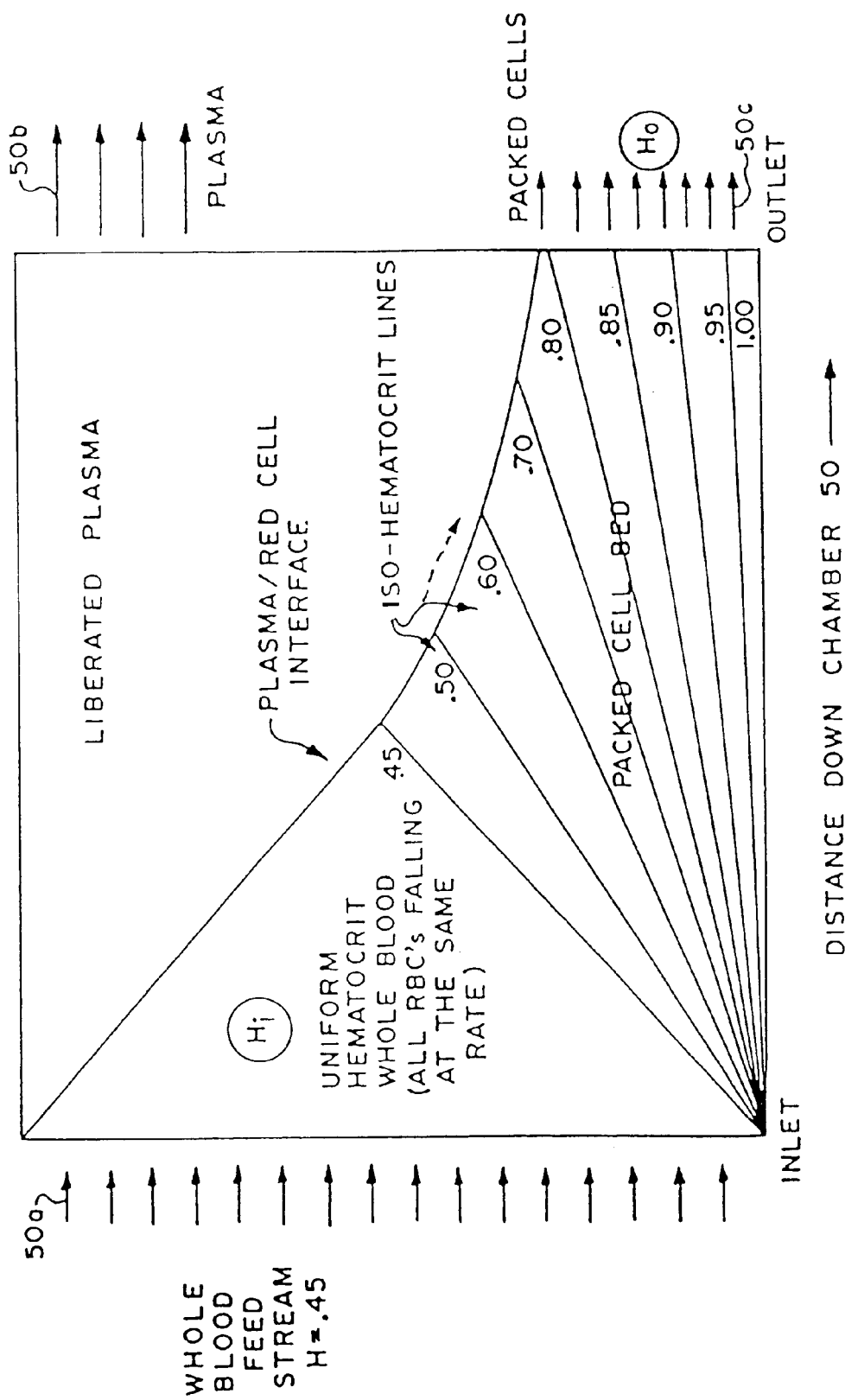

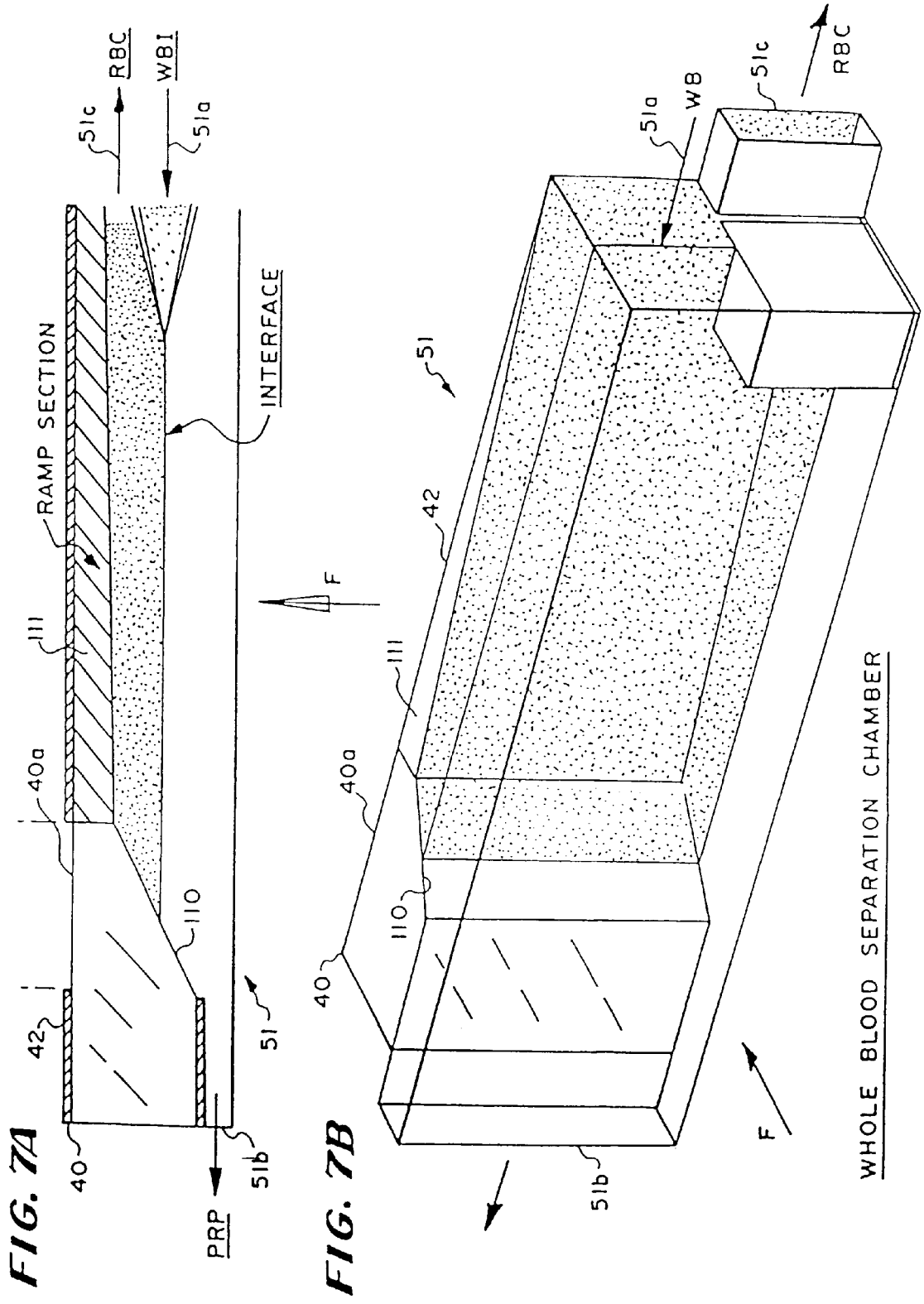

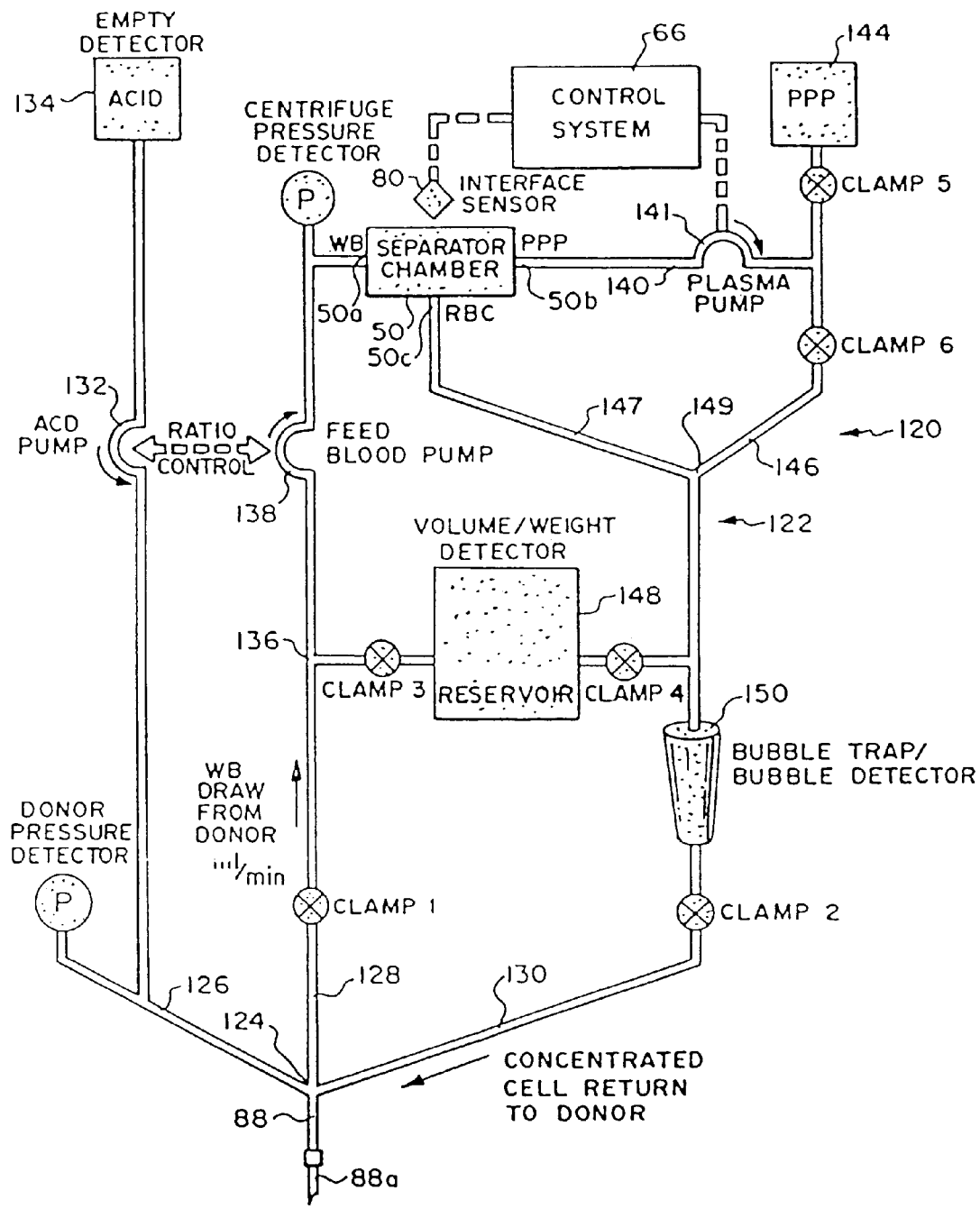

METHODS OF COLLECTING A BLOOD PLASMA CONSTITUENT

This is a divisional of application Ser. No. 08/943,750 filed on Oct. 3, 1997, U.S. Pat. No. 5,849,203, which is a divisional of application Ser. No. 08/593,719 filed on Jan. 29, 1996 U.S. Pat. No. 5,693,232; which is a divisional of application Ser. No. 08/199,082 filed Feb. 22, 1994, U.S. Pat. No. 5,494,578; which is a divisional of application Ser. No. 07/748,244 filed Aug. 21, 1991, U.S. Pat. No. 5,322,620; which is a continuation of application Ser. No. 07/514,995 filed May 26, 1989 (now U.S. Pat. No. 5,104,526); which is a continuation of application Ser. No. 07/009,179 filed Jan. 30, 1987 (now U.S. Pat. No. 4,834,890).

TECHNICAL FIELD

The invention pertains to the field of blood component separation and collection. More particularly, the invention pertains to the collection of platelets or plasma from volunteer donors at temporary sites, remote from medical facilities, with portable lightweight equipment capable of easy transport.

BACKGROUND OF THE INVENTION

The collection of blood from volunteer donors has become a very successful and very refined activity. The development of single needle, single use, disposable blood collection sets has provided a safe, relatively inexpensive and donor comfortable medium for use in the blood collection process. Such sets have made possible large-scale collection of blood from volunteer donors at sites such as church halls, schools or offices which might be remote from medical facilities. The availability of volunteer donors is important in that such donors tend to be relatively healthy. In addition, they provide a potentially much larger reservoir of donatable blood than is available from the available group of paid donors.

In recent years, processing of whole blood from a donor has come to routinely include separating the blood into therapeutic components. These components include red blood cells, platelets and plasma. Various techniques and apparatus have been developed to facilitate the collection of whole blood and the subsequent separation of therapeutic components therefrom.

The collection of platelets or plasma from volunteer donors, as opposed to the collection of whole blood, has not been nearly as successful. As a result, much of the plasma now collected comes from paid donors, as opposed to volunteer donors. It would be very desirable to be able to upgrade the collection of plasma so that it becomes a volunteer based activity to a much greater extent than it is currently.

Various methods are known for the collection of platelets or plasma. For example, a unit of blood can be drawn from a human donor in a conventional fashion and accumulated in a blood bag or other standard collection container. This unit of blood can then be processed by a centrifuge to separate the plasma from the other components of the blood unit. The separated platelets and plasma can subsequently be removed from the blood bag. Although allowing all blood components to be harvested, this process has the disadvantage that the donor must internally replace the complete unit of blood from which the plasma was extracted. The replacement process can take 6 to 12 weeks during which time the donor cannot again give blood. Further, this process yields only a small portion of available plasma/donor.

In a modification of the above system, plasmapheresis can be performed by centrifugation at the time of donation. The non-plasma portion of the blood is then returned to the donor immediately. While this process allows more frequent donation, often as frequently as once per week, the blood is physically separated from the donor for centrifugation.

Such physical separation is undesirable because of the cost and complexity of systems and procedures that have been developed to minimize the risk of error when several donors are being processed simultaneously. In addition, physical separation of the blood from the donor could potentially raise concerns in the collection staff of exposure to infectous agents in the collected blood if fluid drips or leaks occur.

Separation systems in which the accumulated whole blood is not physically separated from the donor are also known. These can be either batch or continuous systems.

One continuous centrifuge based system is disclosed in Judson et al. U.S. Pat. No. 3,655,123 entitled "Continuous Flow Blood Separator." The system of the Judson et al. patent uses two needles, an outflow needle and an inflow needle. Whole blood is drawn from a donor via the outflow needle. The whole blood fills a buffer bag. Blood from the buffer bag drains, under the force of gravity into a centrifuge. The system of the Judson et al. patent uses the centrifuge to separate blood components. The plasma can be collected in a container. The red blood cells can be returned to the donor via the inflow needle.

Various systems are known that utilize annular separation chambers for plasma pheresis. For example, U.S. Pat. No. 4,531,932 to Luppin et al. entitled Centrifugal Plasmapheresis Device discloses a system which incorporates a centrifuge with a rotating annular rotor. A centrally located rotating seal couples stationary fluid flow lines to the rotating rotor.

Whole blood is drained from a donor, passed through the rotating seal and subjected to separating rotational forces in the rotating rotor. Separated plasma is drawn off and concentrated whole blood cells are passed back through the rotating seal and returned to the donor.

Related types of systems which incorporate rotatable, disposable annular separation chambers coupled via rotary seals to stationary tubing members are disclosed in U.S. Pat. Nos. 4,387,848; 4,094,461; 4,007,871; and 4,010,894.

One consideration in the processing of whole blood is the requirement that the processing take place under sterile conditions. A second consideration is the requirement that processing take place so as to maximize storage life. Unless the processing takes place within a single sealed system, the permitted storage duration and usable lifetime of the blood components is substantially shortened. Components processed within a sealed system can be stored for four to six weeks or longer before use. On the other hand, whole blood or components thereof must be used within 24 hours if the system seal is broken.

To promote the desired ends of sterile processing within a single sealed system, a family of dual member centrifuges can be used to effect cell separation. One example of this type of centrifuge is disclosed in U.S. Pat. No. RE 29,738 to Adams entitled "Apparatus for Providing Energy Communication Between a Moving and a Stationary Terminal."

As is now well known, due to the characteristics of such dual member centrifuges, it is possible to rotate a container containing a fluid, such as a unit of donated blood and to withdraw a separated fluid component, such as plasma, into a stationary container, outside of the centrifuge without using rotating seals. Such container systems can be formed as closed, sterile transfer sets.

The Adams patent discloses a centrifuge having an outer rotatable member and an inner rotatable member. The inner member is positioned within and rotatably supported by the outer member.

The outer member rotates at one rotational velocity, usually called one omega, and the inner rotatable member rotates at twice the rotational velocity of the outer housing or two omega. There is thus a one omega difference in rotational speed of the two members. For purposes of this document, the term "dual member centrifuge" shall refer to centrifuges of the Adams type.

The dual member centrifuge of the Adams patent is particularly advantageous in that, as noted above no seals are needed between the container of fluid being rotated and the non-moving component collection containers. The system of the Adams patent, provides a way to process blood into components in a single, sealed, sterile system wherein whole blood from a donor can be infused into the centrifuge while the two members of the centrifuge are being rotated.

An alternate to the apparatus of the Adams patent is illustrated in U.S. Pat. No. 4,056,224 to Lolachi entitled "Flow System for Centrifugal Liquid Processing Apparatus." The system of the Lolachi patent includes a dual member centrifuge of the Adams type. The outer member of the Lolachi centrifuge is rotated by a single electric motor which is coupled to the internal rotatable housing by belts and shafts.

U.S. Pat. No. 4,108,353 to Brown entitled "Centrifugal Apparatus With Oppositely Positioned Rotational Support Means" discloses a centrifuge structure of the Adams type which includes two separate electrical motors. One electric motor is coupled by a belt to the outer member and rotates the outer member at a desired nominal rotational velocity. The second motor is carried within the rotating exterior member and rotates the inner member at the desired higher velocity, twice that of the exterior member.

U.S. Pat. No. 4,109,855 to Brown et al. entitled "Drive System For Centrifugal Processing Apparatus" discloses yet another drive system. The system of the Brown et al. patent has an outer shaft, affixed to the outer member for rotating the outer member at a selected velocity. An inner shaft, coaxial with the outer shaft, is coupled to the inner member. The inner shaft rotates the inner member at twice the rotational velocity as the outer member. A similar system is disclosed in U.S. Pat. No. 4,109,854 to Brown entitled "Centrifugal Apparatus With Outer Enclosure".

Centrifuges of the type disclosed in the above indentified Brown et al. and Brown patents can be utilized in combination with a sealed fluid flow transfer set of the type disclosed in U.S. Pat. No. 4,379,452 to DeVries. The disclosure of the DeVries patent is incorporated herein by reference. The set of the DeVries patent incorporates a blood collection container that has a somewhat elongated shape similar to those of standard blood collection sets. One embodiment of this combined system is the CS3000 cell separator system marketed by Travenol Laboratories, Inc.

The CS3000 incorporates a dual member centrifuge in combination with a sealed set of the type disclosed in DeVries. This is a continuous system that requires the donor to receive two needle punctures. Such systems have been extensively used in blood centers for plasma and platelet pheresis.

The CS3000 is a large and expensive unit that is not intended to be portable. Further, the DeVries type transfer sets are quite complex to install and use. They are also an order of magnitude more expensive than a standard, multi-container blood collection set.

A further alternate to the Adams structure is illustrated in U.S. Pat. No. 4,530,691 to Brown entitled "Centrifuge With Movable Mandrel." The specification and figures of this Brown patent are hereby incorporated by reference herein. The centrifuge of this latter Brown patent also is of the Adams-type. However, this latter centrifuge has an exterior member which is hinged for easy opening. When the hinged upper section is pivoted away from the bottom section, it carries the rotatable inner member along with it.

The inner member supports a receiving chamber with a spring biased mandrel which continually presses against a sealed, blood containing container positioned within the receiving chamber. The system of this latter Brown patent also discloses the use of two separate electric motors to rotate the inner and outer members. The motors are coupled to a control system.

There thus continues to be a need for methods and related apparatus of platelet or plasmapheresis which can readily be used with volunteer donors at various temporary locations. This method and related apparatus should be usable by technicians with a level of skill commensurate with the level of skill now found at volunteer-based blood collection centers. Further, both the method and related apparatus should be readily portable to locations such as churches or schools where blood collection centers are temporarily established. Preferably the apparatus will be essentially self-contained. Preferably, the equipment needed to practice the method will be relatively inexpensive and the blood contacting set will be disposable each time the plasma has been collected from a single donor.

SUMMARY OF THE INVENTION

In accordance with the invention, a method is provided of continuously separating a selected component from a fluid. The method includes providing an elongated flexible separation chamber which has an input port. The separation chamber or member has at least one output port.

A first fluid flow conduit, a plastic tubing member for example, is coupled at one end to the input port. A second fluid flow conduit, also a plastic tubing member, is coupled to the output port.

A centrifuge is provided which has a hollow cylindrical receiving chamber. The separation member is placed in the receiving chamber adjacent an interior curved peripheral wall thereof. Distal ends of the two tubing members are brought out to a fixed location.

The centrifuge, including the receiving chamber is then rotated at predetermined first and second rates. Simultaneously, an input fluid flow is provided at the fixed distal end of the first fluid flow conduit. The input fluid flow partly fills the separation member. The input fluid is separated in these separation member by centrifugal forces. An interface is formed between a portion of the separated fluid component and a portion of the residual fluid. The interface is formed adjacent a selectively oriented surface of the receiving chamber.

The location of the interface on the surface is sensed. A portion of the separated component is withdrawn through the output port via the second fluid flow conduit and out the fixed distal end thereof in response to the interface being sensed at a predetermined location.

The withdrawing step can include pumping the separated fluid component through the second fluid flow conduit. The separated component can then be accumulated in a component container.

In one embodiment of the invention, a blood collection and component separation set is provided. The set includes an elongated flexible separation chamber which is formed with at least one interface region thereon. The interface region is, at least in part, transmissive of radiant energy. The chamber has a whole blood input port, a separated component output port and a residual fluid output port. The separated component can be for example plasma or platelets.

First, second and third fluid flow conduits are provided, each of which, for example being a plastic tubular member. Each fluid flow conduit has a proximal end coupled to a respective input or output port of the separation chamber.

The first fluid flow conduit is coupled to the whole blood input port. A distal end thereof can in turn be coupled to donor collection means which can include a piercing cannula. The second fluid flow conduit is coupled to the selected component output port. A distal end thereof can be coupled to a collection container. The third fluid flow conduit is coupled to the residual fluid output port.

In accordance with this embodiment of the invention, a quantity of whole blood can be withdrawn from a donor and drawn into the separation chamber. The whole blood can be separated into plasma or platelets and packed red blood cells in the separation chamber. The plasma or platelets can be drawn off or pumped into the component collection container. The packed red blood cells can then be collected or returned to the donor. The process can then be repeated a number of times until the desired quantity of plasma or platelets has been collected.

This embodiment requires that the donor only receive a single needle puncture. In addition, if the concentrated red blood cells and plasma are to be returned to the donor, the donor is never physically disconnected from the pheresis system until that return process has been completed.

In yet another embodiment of the invention, platelets can be separated from the plasma and collected in a second component collection container. In this embodiment, the platelets can be accumulated in the separation chamber while the plasma is being drawn off. Subsequently, after the plasma has been drawn off the platelets can be drawn off and collected.

The blood collection set can be formed with a single cannula which is used for both drawing whole blood and returning packed red blood cells to the donor. Alternately, if desired, the set can be configured as a two cannula set with one cannula used for withdrawing whole blood and a second cannula used for returning packed red blood cells to the donor.

In yet another embodiment of the invention, the separation chamber can be formed in two parts. The first part can include the whole blood input port and the packed red blood cell output port. This first part is in fluid flow communication with a second part. Platelet rich plasma separated from the whole blood in the first part flows into the second part and is in turn separated from the platelets therein. The plasma can then be drawn off into a collection container or returned to the donor along with the red blood cells. The platelets can continue to accumulate in the second part. Additional quantities of whole blood can be drawn from the donor and passed through the separation chamber. Subsequently, the collected platelet concentrate can be sealed in the second part.

The receiving chamber in the dual member centrifuge can be formed with an annular slot. The slot receives and supports the elongated separation chamber.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIG. 4 is a sectional view taken along plane 4—4 of FIG. 3B;

FIG. 5A is a top plan view of a separation chamber in accordance with the present invention illustrating the pheresis process;

FIG. 6 is a graph of varying hematocrit of fluid in a rotating separation chamber as a function of distance along the separation chamber in accordance with the present invention;

FIG. 7A is a top plan view of an alternate separation chamber in accordance with the present invention;

FIG. 7B is a perspective view of the alternate separation chamber of FIG. 7A;

FIG. 8 is a schematic fluid flow circuit illustrating an alternative fluid flow transfer set and method of practicing the present invention;

DETAILED DESCRIPTION OF THE PREFERRED EMBODIMENT

Figure 1:
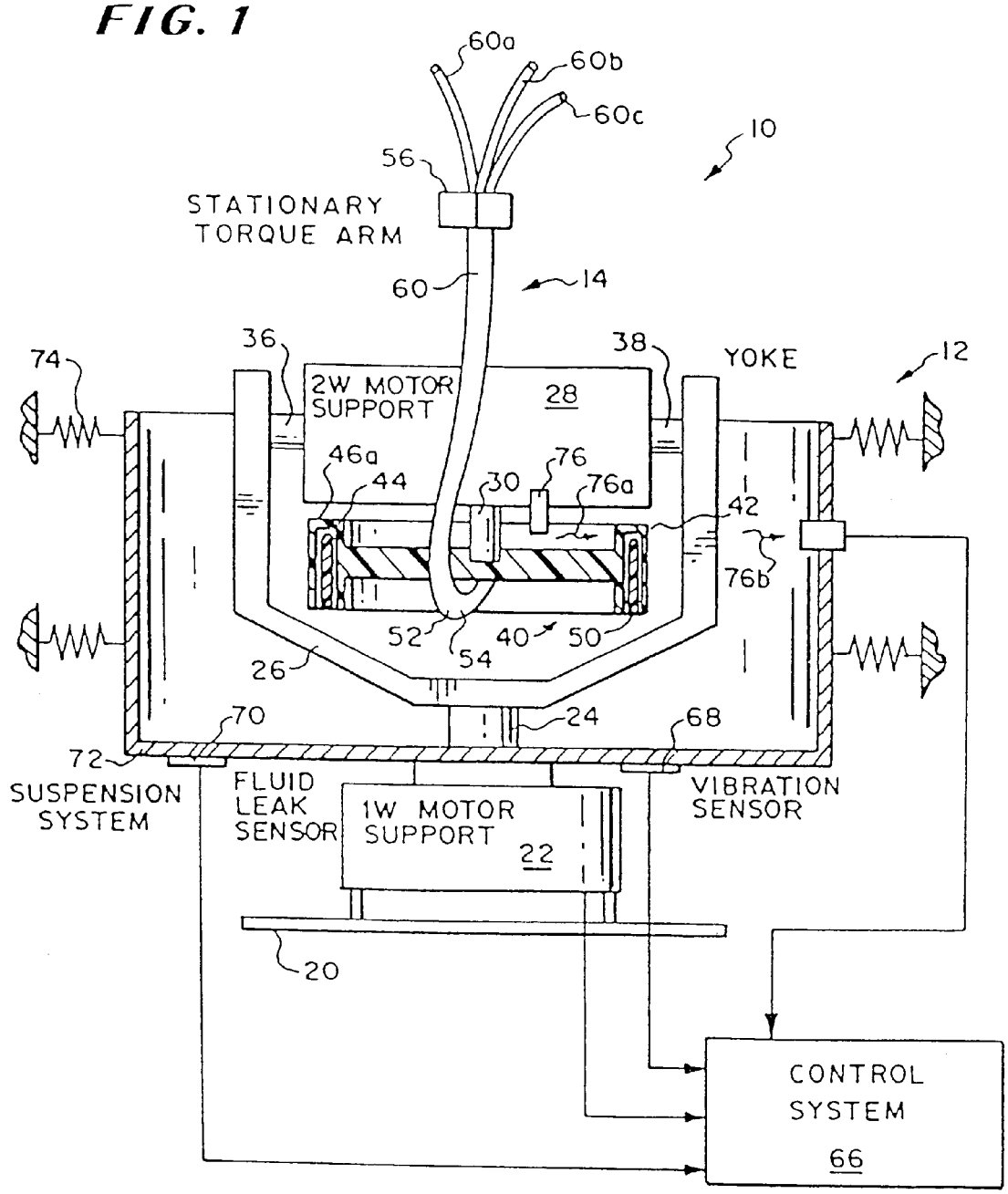
FIG. 1 is a schematic view, fragmented and partly in section of a system and method of pheresis in accordance with the present invention.

While this invention is susceptible of embodiment in many different forms, there is shown in the drawing and will be described herein in detail specific embodiments thereof with the understanding that the present disclosure is to be considered as an exemplification of the principles of the invention and are not intended to limit the invention to the specific embodiments illustrated.

FIG. 1 illustrates a readily transportable system 10 in accordance with the present invention. The system 10 includes a relatively light-weight dual member centrifuge 12 and an associated fluid flow transfer set 14.

The dual member centrifuge 12 is of the Adams type having a stationary support 20 on which is mounted a first motor 22. The first motor 22 has a rotary output shaft 24 which rotates at a first angular velocity conventionally referred to as one omega. Fixedly attached to the rotary shaft 24 is a yoke 26. The yoke 26 supports a second electric motor 28. The electric motor 28 has a rotary output shaft 30. The shaft 30 rotates at an angular velocity twice that of the shaft 24, conventionally referred to as two omega. The motor 28 is pivotably attached to the yoke 26 at pivot points 36 and 38.

Affixed to the rotating shaft 30 is a cylindrical receiving chamber 40. The details of the chamber 40 are illustrated in detail in FIG. 2. The receiving chamber 40 is rotated by the shaft 30. The chamber 40 includes a region 40a that is transparent to selected, incident radiant energy. The chamber 40 has a cylindrical exterior peripheral region 42. Spaced apart from the exterior region 42 is a generally cylindrical interior peripheral region 44. Between the exterior region 42 and the interior region 44 is a selectively shaped annular slot 46. The slot 46 has a closed end 46a. The slot 46 slidably receives a separation chamber 50. The chamber 40 has an exterior diameter on the order of six inches and an internal length on the order of 2.3 inches. The slot 46 has a length on the order of 2.1 inches. The width of the slot 46 is on the order of 0.2 inches.

The separation chamber 50 is in fluid flow communication via a flexible multi-channel conduit 52 with the remainder of the set 14. A proximal end 54 of the flexible fluid flow conduit 52 is coupled to the separation chamber 50.

Figure 3A:
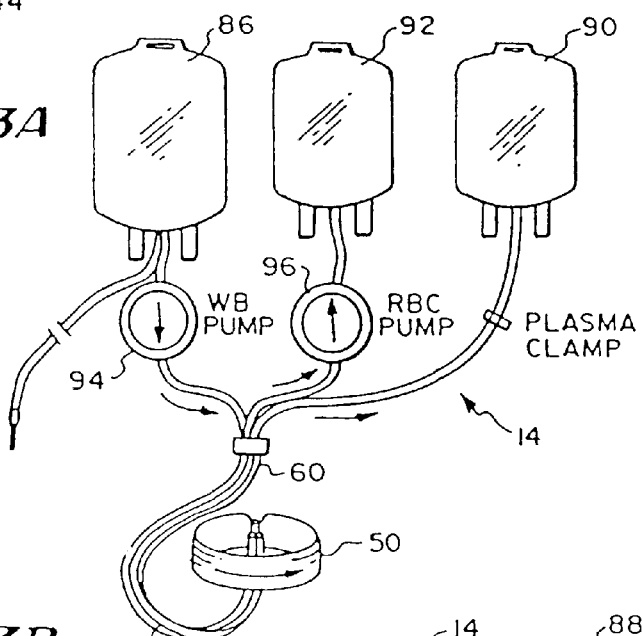
FIGS. 3A and 3B illustrate schematically a particular transfer set and method of pheresis in accordance with the present invention.
Figure 3B:
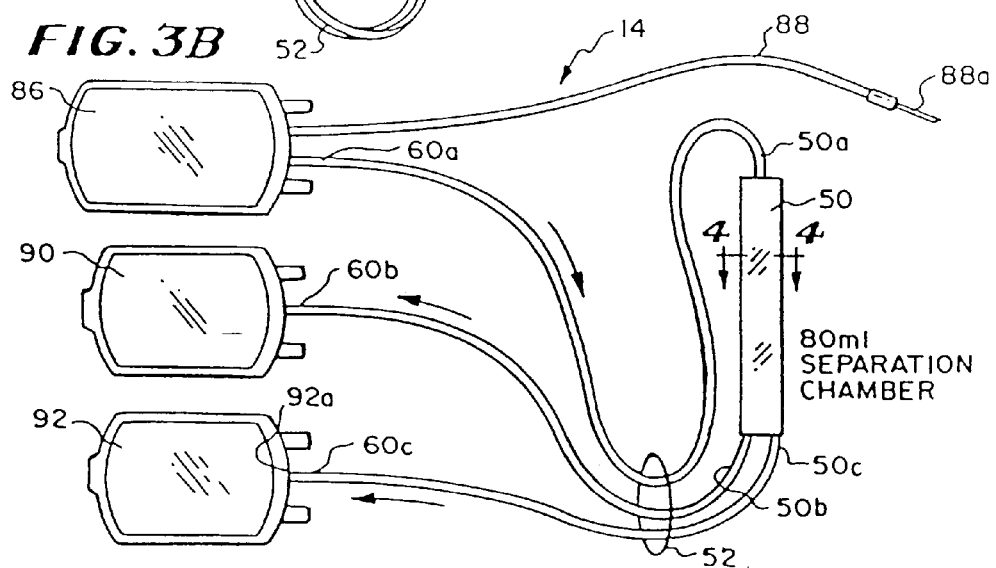

The fluid flow conduit 52 is supported by a stationary torque arm 56. The use of such torque arms is well known to those skilled in the use of dual member centrifuges of the Adams type. A distal end 60 of the fluid flow conduit 52 separates into a plurality of discrete flexible conduits 60a, 60b and 60c. The distal ends 60a, 60b and 60c are each in fluid flow communication with a respective container as seen in FIGS. 3a and 3b.

The conduits 60a, 60b and 60c could be formed of various flexible, medical grade plastics.

The system 10 also includes a control system 66 which is coupled to the motors 22 and 28. Control systems for use with dual member centrifuges of the Adams type are known in the art. One type of suitable control system is a proportional-integral-differential control system. Various of the above noted patents disclose a variety of ways to rotate and control dual member centrifuges.

The control system 66 receives feedback from vibration and fluid leak sensors 68 and 70. The sensors 68 and 70 are fixedly supported by a stationary suspension system 72. The system 72 can be connected to resilient members 74 to stabilize the centrifuge 12 during operation.

A source of radiant energy 76 is affixed to the 2ω motor 28. The source 76 directs a beam of radiant energy 76a toward the radiant energy transmitting region 40a of the rotatable chamber 40. The region 40a permits the beam of radiant energy 76a to inpinge on an interface region of the separation chamber 50. A portion 76b of the beam 76a will pass through the interface region of the separation chamber 50 and emerge to be detected at an interface sensor 80.

The source 76 could be any emitter of radiant energy such as infrared or incandescent light. The sensor 80 could be any compatible energy sensitive detector. The interface sensor 80 can be used to detect the location of the interface between the separated plasma and packed red blood cells in the separation chamber 50 during the centrifugation process. The sensor 80 is also coupled to the control system 66.

Figure 2:
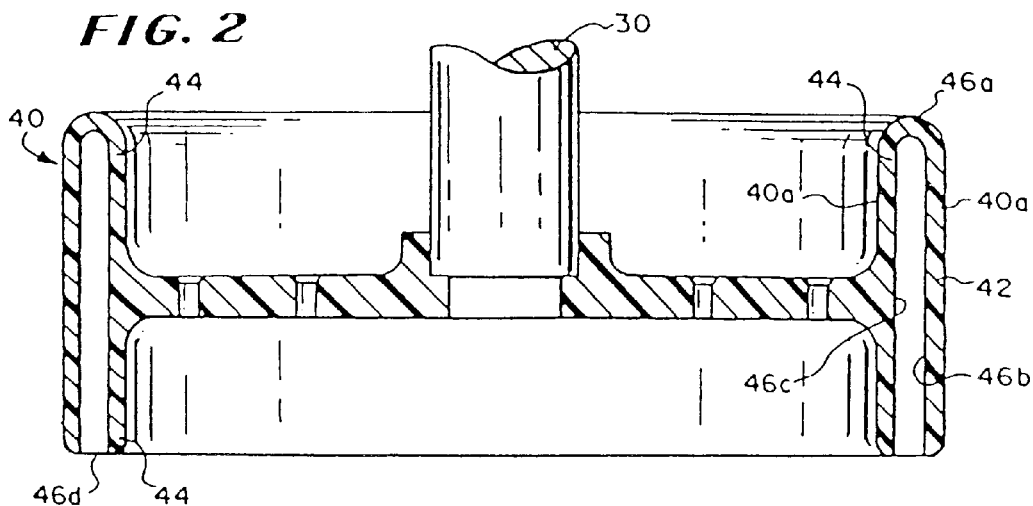
FIG. 2 is an enlarged sectional view of the receiving chamber of FIG. 1.

FIG. 2 illustrates the shape of the slot 46 in the receiving chamber 40. The slot 46 has two spaced apart annular surfaces 46b, 46c. This spacing is on the order of 0.2 inches. The slot 46 has a downwardly oriented opening 46d. The separation chamber 50 is slid into the slot 46 via the opening 46d. If necessary, the opening 46d can be covered by a metal cover to initially retain the separation chamber 50 in position. Once the chamber 40 is rotated and the chamber 50 has been filled with fluid, the rotational forces set up adequate frictional forces such that the separation chamber 50 will be locked in place.

The chamber 40 can be molded of polycarbonate, a transparent plastic. The radiant energy beam 76a readily passes through this material. The chamber 40 can be selectively painted or masked so as to limit those regions through which the radiant energy 76a can pass.

FIGS. 3a and 3b schematically illustrate the details of the fluid transfer set 14 as well as one mode of using same. In FIGS. 3a and 3b arrows along a conduit or tubing member indicate a direction of fluid flow.

The set 14 in addition to the separation chamber 50 and the multi-channel conduit 52 includes a whole blood collection container 86. Attached to the collection container 86 is a draw conduit 88 which terminates at a free end in a draw cannula 88a. The draw cannula 88a is intended to be inserted into a vein of a donor. The set 14 also includes a plasma collection container 90 and a red blood cell nutritive container 92.

The solution in the container 92 is of a known type which provides nutrients to packed red blood cells subsequent to the plasma pheresis process. Contents of such solutions include dextrose, sodium chloride, mannitol and adenine. One appropriate solution is marketed by Travenol Laboratories, Inc. under the trademark ADSOL. The container 92 is sealed with a frangible member 92a which can be broken at an appropriate point in the plasma pheresis process.

The set 14 is initially used to collect a unit of blood in the whole blood collection container 86 using standard procedures. Once the unit of whole blood 86 has been collected, the cannula 88a is removed from the arm of the donor and the tubing 88 is closed by heat sealing. The set 14 is now a closed sterile system. The separation chamber 50 is positioned in the slot within the rotatable receiving chamber 40. The separation chamber 50 can then be rotated.

A whole blood pump 94 can be utilized to meter whole blood from the container 86 into the chamber 50 for separation into concentrated red blood cells and plasma. The plasma can be withdrawn after separation into the container 90. A second pump 96 can be used to pump the concentrated red blood cells into the container 92 containing the nutritive solution. The containers 90 and 92 can then be closed by heat sealing and separated from the remainder of the set 14.

While the set and method illustrated in FIGS. 3a and 3b are primarily suited for processing of whole blood on a batch basis, one of the advantages of the present invention lies in the fact that it should be possible to separate to a great extent the white cells from the plasma. It is known that from time to time the white cells from a donor infused into a receipient can cause an adverse reaction. Hence, removal of these white cells would be both desirable and beneficial.

In a preferred mode, the separation chamber 50 has a volume on the order of 80 to 90 ml. The preferred separation centrifugation speeds are in a range on the order of 3800 to 4200 rpm.

FIG. 4, a sectional view taken along plane 4—4 of FIG. 3b, illustrates the overall shape of the chamber 50 prior to the centrifugation process. The chamber 50 can be formed of a single plastic sheet member. That member is folded on itself and sealed in a region 51. An internal volume 51a results. The fluid being separated flows in this volume.

Figure 5B:
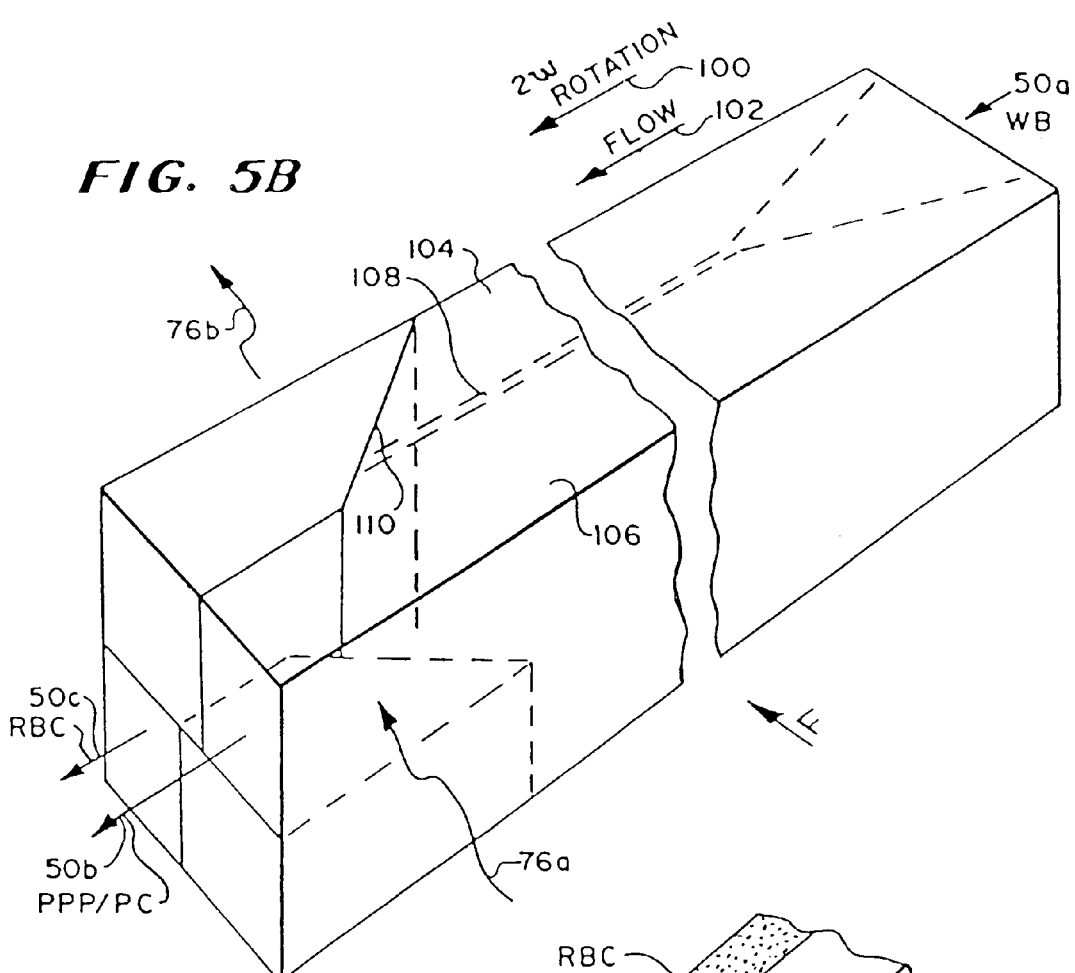
FIG. 5B is a perspective view of the separation chamber and pheresis process illustrated in FIG. 5A.
Figure 5C:
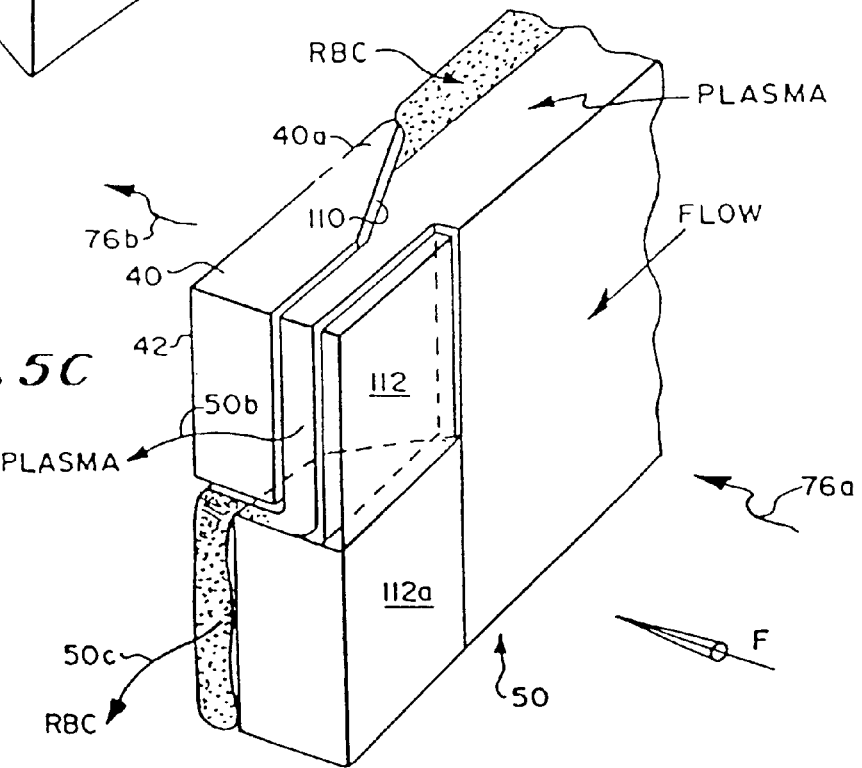
FIG. 5C is a perspective view of an alternate embodiment of the separation chamber illustrating the pheresis process therein.

FIGS. 5A through 5C schematically illustrate the separation process as the separation chamber 50 is being rotated. As is illustrated in FIGS. 5A–5C the chamber 40 and the separation chamber 50 are rotated in a direction 100. Whole blood is infused at the input port 50a and flows into the separation chamber 50 in a direction 102. The whole blood input port 50a is positioned centrally with respect to the centrifugal force field F.

Under the influence of the centrifugal force field F, the whole blood separates into high density packed red blood cells in an outer annular region 104 adjacent the maximum centrifugal force region 42 of the rotatable chamber 40. Lower density plasma separates out into an inner annular region 106 adjacent a relatively lower centrifugal force region adjacent the inner region 44. Between the outer annular region 104 of packed red blood cells and the inner annular region 106 of plasma, a substantially smaller layer 108 of platelets forms.

A surface 110 can be provided which is at a predetermined angle with respect to the direction of flow 102. The surface 110 provides a very sharp and highly transmissive interface between the region of plasma 106 and the region of packed red blood cells 104. The incident radiant energy 76a passes through the surface member 110, which is essentially transparent thereto, and out the transparent region 40a of the chamber 40 as the output radiant energy beam 76b. When sensed by the interface sensor 80 the precise location of the interface between the plasma in the region 106 and the packed red blood cells in the region 104 can be determined.

The output port 50b for the platelet rich plasma is located adjacent the low force inner surface 50d of the separation chamber 50. Platelet poor plasma can be withdrawn therefrom under the control of the control system 66 in response to the sensed position of the interface between the red blood cells and the plasma on the surface 110.

The residual fluid output port 50c from which the packed red blood cells can be withdrawn is positioned adjacent the relatively high force outer surface of the separation chamber 50 adjacent the outer peripheral surface 40a.

The transparent surface 110 can be formed as part of the separation chamber 50. Alternatively, the surface 110 can be affixed to the rotatable chamber 40. In this instance, a region of the chamber 50 can be positioned adjacent thereto.

Depending on the location of the annular region 108 of platelets with respect to the surface 110, the system 10 can operate in several different modes.

If the location of the region 108 has moved adjacent an interior end 110a of the surface 110, the platelets will spill through the port 50b resulting in platelet rich plasma as the separated fluid component.

If the region 108 is centrally located as in FIG. 5A, platelets will accumulate in the chamber. Platelet poor plasma will then flow out the port 50b. In this mode, the plasma continually flows inwardly through the platelet region 108. This fluidizes the platelets and minimizes sedimenting and aggregating of the platelet concentrate.

In a third mode of operation, the platelet region 108 can be positioned adjacent an outer regon 110b. In this instance, the platelets will be swept out of the chamber, via the port 50c with the packed red blood cells.

As illustrated in FIG. 5C, a dam 112 can also be provided adjacent the plasma output port 50b. As is discussed subsequently, the dam 112 is effective to retain a fluid, such as air, in the chamber 50 during start up of the centrifugation process.

As was the case with the surface 110, the dam 112 can be integrally formed with either the separation chamber 50 or can be formed as part of the rotatable chamber 40.

It will be understood that FIGS. 5a through 5c are schematic in nature and are intended to illustrate the separation process. The shape of the separation chamber 50 during the pheresis operation will be determined by the shape of the slot 46.

The graph of FIG. 6 illustrates the expected change of hematocrit as whole blood is infused through the input port 50a and travels along the rotating separation chamber 50. Assuming an input hematocrit on the order of 0.45, the hematocrit of the output packed red blood cells ranges between 0.80 and 1.0. One of the functions of the nutritive mixture provided in the container 92 is to restore the hematocrit of the packed red blood cells to a value such that infusion into a receipient is possible.

FIGS. 7A and 7B illustrate schematically an alternate separation chamber 51. In the separation chamber 51, whole blood is injected into the chamber at a centrally located input port 51a. Unlike the separation chamber 50, an output port 51c for the concentrated red blood cells is provided at the same end of the chamber 51 as is the whole blood input port 51a. In this embodiment, the red blood cells are withdrawn in the opposite direction as the input flow of the whole blood. The output port 51c is located adjacent the high force outer peripheral wall of the separation chamber 51. Thus, there are two directions of flow of fluid within the chamber 51.

The chamber 51 also includes a supplemental ramp 111 to urge or push the packed cells towards the packed cell removal port 51c. This flow is opposite the flow of whole blood 51a. The ramp 111 may be integrally formed as part of the separation chamber 51. Alternately, the ramp 111 can be formed as part of the rotatable member 40.

FIG. 8 illustrates yet another system 120 which incorporates the elongated flexible separation chamber 50. The system 120 is a centrifugely based pheresis system which can provide as a separated component from whole blood either platelet poor plasma or platelet concentrate.

The system 120 includes a fluid flow transfer set 122 which is useable in conjunction with the dual member centrifuge 12. The transfer set 122 includes the draw conduit 88 with the associated cannula 88a. In the set 122, the cannula 88a is used for drawing whole blood from a donor and for returning concentrated red blood cells and/or plasma to the donor during the pheresis operation. The system 120 is intended to be coupled to the donor continuously throughout the entire pheresis operation.

The draw/return conduit 88 is coupled at a junction connector 124 to respective tubing lines 126, 128 and 130. The tubing member 126 is coupled via an anticoagulant pump 132 to a container of anticoagulant 134. The tubing member 128 is coupled via a connector 136 and a feed blood pump 138 to the whole blood input port 50a of the separation chamber 50.

The separated component output port 50b of the separation chamber 50 is coupled via a tubing member 140 to a plasma pump 141. A tubing member 142 is coupled alternately either to a separated component container 144 or a tubing member 146. The member 146 feeds either a reservoir 148 or a bubble trap/bubble detector, 150 in the return conduit line 130. Clamps 1 through 6 would be manually opened and closed to regulate the desired directions of flow.

The residual output port 50c is coupled via a tubing member 147 and a junction member 149 to the bubble trap/bubble detector 150.

In operation, the set 122 would be coupled to the donor by means of the cannula 88a. The chamber 50, as previously discussed, would be positioned in the receiving chamber of the dual member centrifuge 12. Clamps 1, 4, and 5 would be opened. Clamps 2, 3 and 6 would be closed.

Whole blood would be drained from the donor via conduit 128. Anticoagulant would be simultaneously infused into the whole blood via the conduit 126. The feed blood pump 138 would draw the blood from the donor at approximately a 70 ml per minute rate. The pump 138 would also supply the drawn blood to the input port 50a of the rotating separation chamber 50 at the same rate.

The rotating separation chamber 50 would separate the whole blood into platelet poor plasma at the output port 50b and red blood cells at the output port 50c. Red blood cells from the output port 50c would be accumulated in the reservoir 148 simultaneously with platelet poor plasma being accumulated in the container 144.

When the volume and weight detector associated with the reservoir 148 indicates that a maximum extracorporeal volume has been accumulated therein, clamps 1, 4 and 5 would be closed. Clamps 2, 3 and 6 would be opened.

The concentrated cells in the reservoir 148 would be pumped, via the feed pump 138, through the separation chamber 50 a second time. Output from the separation chamber 50 via conduits 140 and 147 would be passed through the bubble trap 150 and, via the conduit 130, returned through the cannula 88a to the donor. When the weight and volume detector indicated that the reservoir 148 was sufficiently empty, the draw process would be reinitiated.

Hence, the system 120 would be capable of accumulating platelet poor plasma in the container 144. In addition, the platelets would be accumulated in the region 108 of the separation chamber 50. Subsequent to the plasma having been collected, the container 144 can be replaced and the platelets could be drawn off and accumulated in the replacement container.

Densities of platelets which could be accumulated and drawn off in this fashion range from 200 billion to 300 billion cells in 100 ml of fluid. Such densities might take 3 to 4 cycles of whole blood drawn from the donor to build up the necessary platelet concentration in the separation chamber 50.

Alternately, the platelet poor plasma could be pumped into the reservoir 142 and returned after the second pass to the donor. The platelet concentrate can then be accumulated in the container 144.

Figure 9:
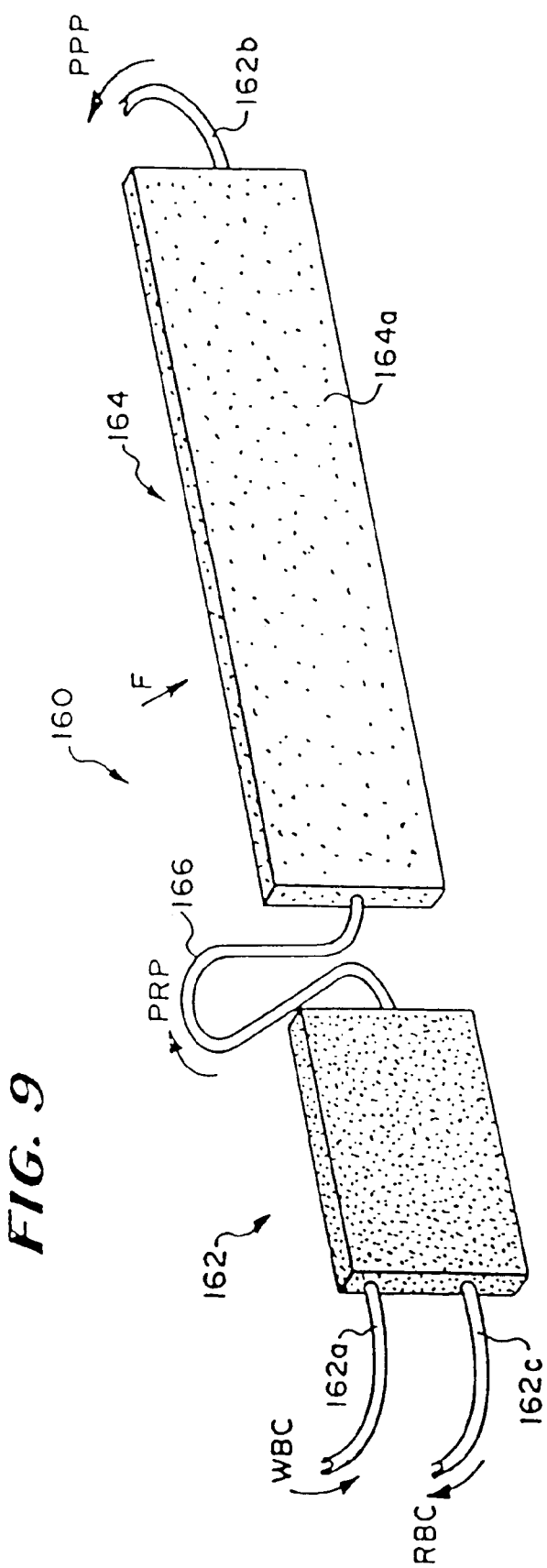
FIG. 9 is a schematic perspective view of a two part separation chamber.

FIG. 9 illustrates yet another separation chamber 160. The separation chamber 160 has two fluid separating portions 162 and 164. The fluid separating portion 162 includes a whole blood input port 162a centrally located at an input end of the portion 162. A concentrated red blood cell output port 162c is also provided adjacent the input port 162a. The portion 162 thus includes whole blood flowing into the region and packed red blood cells flowing out of the region. The portion 162 could have a relatively small volume on the order of 20–30 ml.

Separated platelet rich plasma can be drawn out of the portion 162 via a conduit 166. The platelet rich plasma can then be separated in the second portion 164 into platelet poor plasma and platelets. The platelets accumulate in the second portion 164 along the outer, high force, wall 164a. The second portion 164 includes an output port 162b. The platelet poor plasma can be returned to the donor. The portion 164 can have a volume on the order of 50–60 ml.

Figure 10:
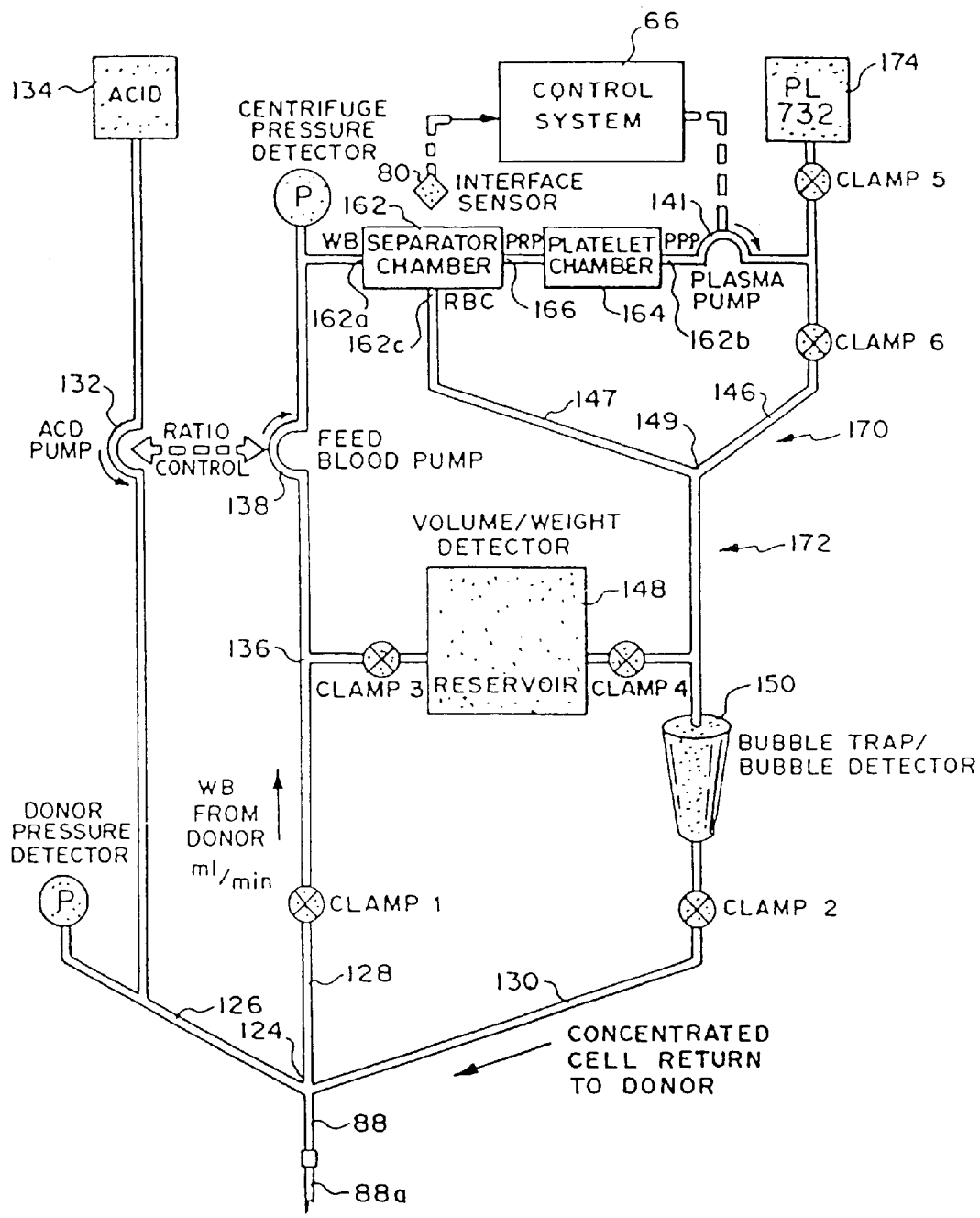
FIG. 10 is a schematic fluid flow circuit illustrating an alternative fluid flow transfer set and method of practicing the present invention.

FIG. 10 illustrates a system 170 usable for platelet pheresis. The system 170 incorporates a single use disposable fluid transfer set 172. The set 172 includes the two part separation chamber 160 of FIG. 9. Other elements of the set 172 which correspond to elements of the previously discussed set 122 have been given identical identification numerals.

The two part chamber 160 would be positioned in the receiving chamber of the dual member centrifuge 12. Clamps 1, 4 and 6 would be opened. Clamps 2, 3 and 5 would be closed. The set 172 could be mounted on an automated fixture which could automatically operate the clamps 1–6.

In operation, the set 172 would be coupled to the donor by means of the cannula 88a. Whole blood would be drawn from the donor by the cannula 88a. The whole blood will flow through the conduit 88, the conduit 128 and, via the feed blood pump 132, would be pumped into the input port 162a of the separation chamber 160 at a 70 ml per minute rate.

Concentrated red blood cells from the output port 162c would flow into the reservoir 148 via the conduit 147. Platelet rich plasma, via the tubing member 166; will flow into the rotating platelet separation chamber 164. Output from the platelet separation chamber 164, via the output port 162b will be platelet poor plasma. The platelet poor plasma will be pumped via the plasma pump 141 in the conduit 146 into the reservoir 148. While the whole blood is passing through the separation chamber portion 162 and the platelet poor plasma is being separated in the platelet chamber 164, platelets will continue to accumulate in the chamber 164.

When the volume and weight detector associate with the reservoir 148 indicates that a maximum extracorporeal volume of drawn blood has accumulated in the set 172, the appropriate detector signal will be generated. The operator or fixture will then close clamps 1 and 4. The operator or fixture will open clamps 2 and 3. Fluid in the reservoir 148 will be pumped via the feed pump 138 through the separation chamber 160 a second time. This fluid includes plasma and packed red blood cells which had previously accumulated therein thus providing a second opportunity to collect those platelets not collected with the first pass. However, with clamp 4 closed, output fluid on the line 147 and the line 166 will pass through the bubble trap/bubble detector 150 through the line 130 and be returned to the donor via conduit 88 and cannula 88a.

When the reservoir 148 has been sufficiently emptied, the volume weight detector will again generate a indicator signal. The operator or fixture will reclose clamps 2 and 3 and reopen clamps 1 and 4 to reinitiate the draw cycle. Whole blood will again be drawn from the donor at the 70 ml per minute rate. This process may be repeated as many times as desired so as to accumulate the desired quantity of platelets in the chamber 164.

Subsequent to the desired quantity of platelets having been accumulated in chamber 164, clamps 1, 3 and 6 can be closed and clamp 5 can be opened. The platelets must then be resuspended, for example, by shaking the platelet chamber 164. Platelets can be pumped from the chamber 164 by the pump 141 into the platelet accumulation container 174. By means of this process, platelets on the order of $4 \times 10^{11}$ cells can be accumulated from a single donor. This represents approximately 90 percent of the platelets which were in the blood drawn from the donor.

Figure 11:
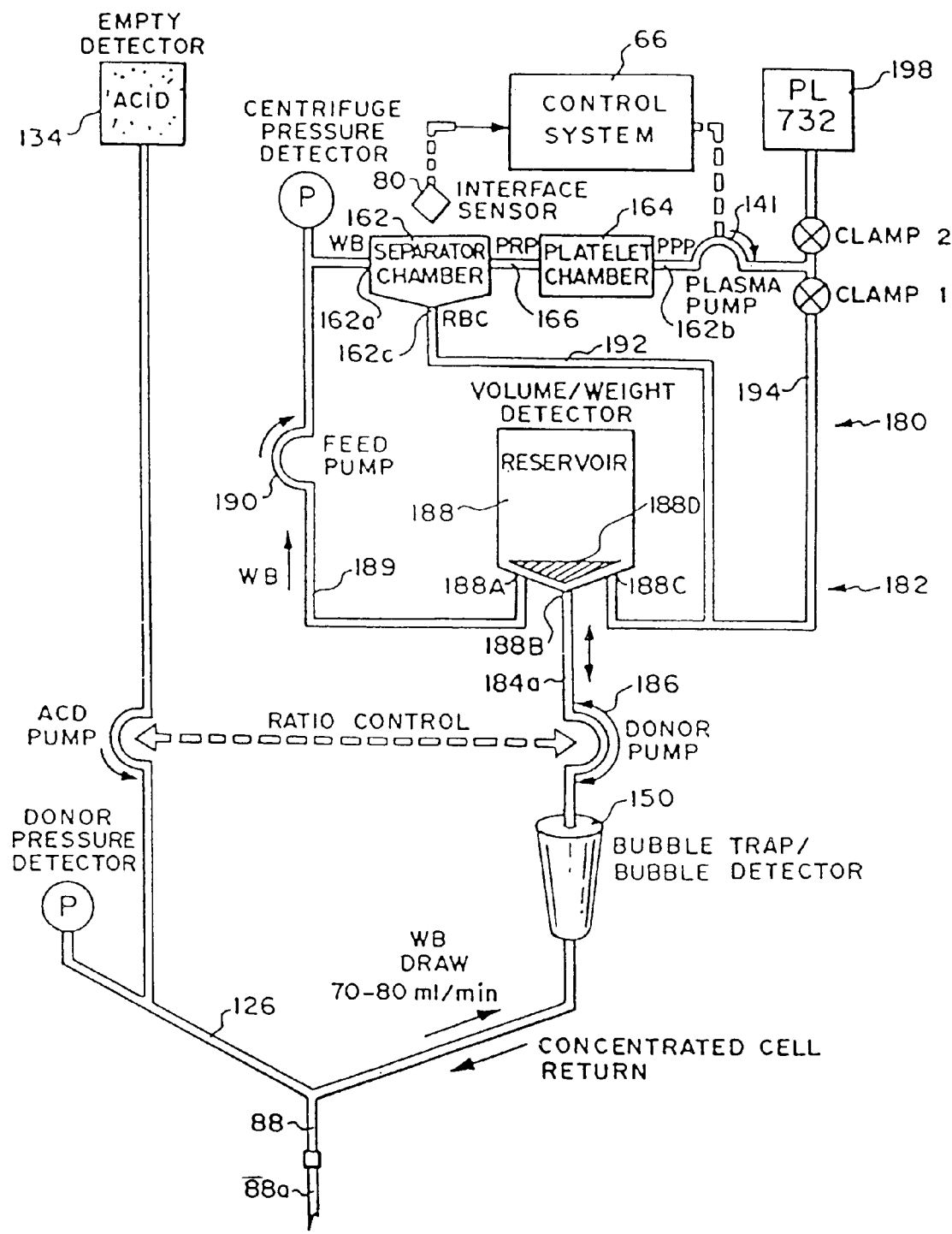
FIG. 11 is a schematic fluid flow circuit illustrating an alternative fluid flow transfer set and method of practicing the present invention.

FIG. 11 illustrates an alternate system 180 which incorporates a disposable fluid flow transfer set 182. The transfer set 182 includes the draw return cannula 88*a* and associated conduit 88. Whole blood is drawn through and concentrated cells are returned through a conduit member 184 which is coupled to an input to the bubble trap/bubble detector 150. Output from the bubble trap/bubble detector 150 via a bidirectional pump 186 flows into a reservoir 188 at an input port 188*b*. A deflector member 188*d* in the container 188 directs and regulates the flow of fluid among the ports 188*a*, 188*b* and 188*c*.

During the draw cycle, whole blood which flows through the conduit 184, the conduit 184*a* and into the input port 188B of the reservoir 188 is deflected by the member 188D and flows out the port 188A. Output whole blood flow from the port 188A via a conduit 189 is pumped by the feed pump 190 at a flow rate of 70–80 ml per minute into the input port 162*a* of the two part separation chamber 160.

Red blood cells separated in the chamber 162 flow via conduit 192 into the input port 188C of the reservoir 188 and are accumulated therein. Assuming clamp 2 is closed and clamp 1 is open, platelet poor plasma separated in the platelet chamber 164 flows via the output port 162*b* and the pump 141 through a fluid flow conduit 194 also into the reservoir 188.

In operation, set 182 would be coupled to the donor by means of the cannula 88*a*. The chamber 160 would be positioned in the receiving chamber of the dual member centrifuge 12. Clamp 1 would be opened and clamp 2 would be closed.

Whole blood would then be drained through the conduit 184 as discussed above at a 70 to 80 ml per minute rate. When the reservoir 188 is filled with a predetermined maximum extracorporeal volume, the volume/weight detector will generate an appropriate signal. At such time, the bidirectional donor pump 186 will be reversed. Fluid will then be drawn from the reservoir 188 out the port 188B via the fluid flow conduit 184*a* and the bubble trap/bubble detector 150 to the fluid flow conduit 184. The fluid will then be returned to the donor via the conduit 88 and the cannula 88*a*.

The return rate of the concentrated cells, including red blood cells and plasma, is on the order of 130 to 150 ml per minute. This substantially increased return fluid flow rate provides the important advantage in that the time necessary to return the concentrated cells to the donor is approximately half of the time required for the draw cycle. While the concentrated cells are being returned to the donor, fluid continues to be pumped from the reservoir 188 via the port 188*a* via the feed pump 190 through the separation chamber 160 and back to the donor via the port 188*c*. Additional volume flow rate can come directly from the reservoir 188. Platelets continue to accumulate in the chamber 164.

The draw cycle can then be reinitiated and an additional quantity of blood drawn from the donor. When the desired quantity of platelets has been accumulated in the chamber 164, clamp 1 can be closed and clamp 2 can be opened. The platelets then need to be resuspended. By means of the pump 141, the platelets in the chamber 164 can then be pumped into the container 198. Quantities of platelets on the order of $4 \times 10^{11}$ cells can be accumulated using the system and apparatus in FIG. 11 in a time interval on the order of 50 minutes.

With respect to the embodiment of FIG. 5C, the use of the dam or shim 112 illustrated therein allows priming of a dry fluid transfer system with whole blood and prevents the occurence of potential air locks which would hinder the flow of plasma and/or platelets in the fluid flow conduits during high speed centrifugation. The shim or dam 112, as noted previously, can be formed as part of the separation chamber 50. Alternately, it can be formed as part of the rotatable receiving chamber 40.

Many of the known cell separation systems require saline priming of the separation chambers prior to the pheresis operation. As a result, it is necessary to supply a container of sterile saline as part of the transfer set. During set up, a frangible in the saline container is broken permiting the saline to flow into the separation chamber driving out any air present therein and providing a liquid filled separation chamber.

The separation chamber 50 of FIG. 5C does not require the use of saline for priming. The various ports have been located on the separation chamber 50, taking into account different fluid densities. The ports are located in different planes of the centrifugal force field F. For example, the input whole blood port 50A is centrally located with respect to the force field. The plasma output port 50B is located adjacent the relatively low force interior wall of the separation chamber 50. The residual fluid output port 50C for the concentrated or packed red blood cells is located adjacent the maximum force exterior wall of the separation chamber 50.

Directing of the fluids to the various output ports is accomplished by means of essentially rigid deflecting members such as the shim or dam 112 adjacent the separated component or plasma output port 50B. A shim or dam 112A is associated with the concentrated red blood cell output port 50C. The interface surface 110 which is illustrated in FIG. 5C formed as part of the outer wall 40*a* of the receiving chamber 40 directs the flow of separated plasma cells.

The dams or shims 112 and 112A are also effective to prevent the flow of air through the plasma port. Since air has a lower density then plasma, a certain amount of air will remain in the inner most region of the separation chamber 50. This air is also compressed at higher centrifuge speeds.

The problem posed by air in the system is a result of pressures induced by the centrifugal force field F. These forces are proportional to the square of the radius of the receiving chamber as well as the square of the rotational velocity of the receiving chamber ana the separation chamber 50 along with the density of the fluid. If air gets into the fluid flow conduit associated with the output port 50B, a pressure drop will occur in that line. This pressure drop may force the plasma pump to clamp the tubing shut and stop the flow of plasma by requiring too high a vacuum in the conduit. Alternately, the pump may degas the plasma.

Overcoming this condition requires that the receiving chamber 40 and separating chamber 50 be slowed down until the plasma pump can overcome this pressure drop. Hence, the use of the saline in the known devices to drive all of the air out of the separation chamber and the related fluid flow conduits. On the other hand, in the embodiment of FIG. 5C the shims or dams 112 and 112*a* prevent movement of the air out of the separation chamber 50 by creating a reservoir which will trap the air within the chamber during a low speed prime with blood. At high speed operation, the centrifugal induced pressure will compress this air away from the dam 112. The presence of a small amount of air in the chamber will not interfere with the pheresis process as long as the air is not permitted to escape into the fluid flow conduits associated with the output port of the chamber.

From the foregoing, it will be observed that numerous variations and modifications may be effected without departing from the true spirit and scope of the novel concept of the invention. It is to be understood that no limitation with respect to the specific apparatus illustrated herein is intended or should be inferred. It is, of course, intended to cover by the appended claims all such modifications as fall within the scope of the claims.

What is claimed is:

1. A method of collecting a blood plasma constituent comprising the steps of:
   (i) conveying whole blood from a donor into a rotating chamber for separation within a centrifugal field into red blood cells and a plasma constituent,
   (ii) collecting the plasma constituent,
   (iii) collecting red blood cells in a reservoir outside the centrifugal field,
   (iv) returning red blood cells in the reservoir to the rotating chamber for separation of residual plasma constituent within the centrifugal field,
   (v) collecting the residual plasma constituent, and
   (vi) returning red blood cells after step (iv) to the donor.

2. A method according to claim 1 wherein step (i) and step (vi) use the same phlebotomy needle.

3. A method according to claim 1 wherein the plasma constituent includes platelets.

4. A method according to claim 1 including the step of separating leukocytes from the plasma constituent.

5. A method of collecting a blood plasma constituent comprising the steps of:
   (i) continuously conveying whole blood from a donor into a rotating chamber for separation within a centrifugal field into red blood cells and a plasma constituent,
   (ii) collecting the plasma constituent during at least part of step (i),
   (iii) collecting red blood cells in a reservoir outside the centrifugal field,
   (iv) returning red blood cells in the reservoir to the rotating chamber for separation of residual plasma constituent within the centrifugal field,
   (v) collecting the residual plasma constituent, and
   (vi) returning red blood cells after step (iv) to the donor.

6. A method according to claim 5 wherein step (i) and step (vi) use the same phlebotomy needle.

7. A method according to claim 5 wherein the plasma constituent includes platelets.

8. A method according to claim 5 including the step of separating leukocytes from the plasma constituent.

* * * * *